United States Patent
Guala

(10) Patent No.: US 9,586,037 B2
(45) Date of Patent: Mar. 7, 2017

(54) VALVED MALE LUER CONNECTOR

(75) Inventor: Gianni Guala, Turin (IT)

(73) Assignee: INDUSTRIE BORLA S.P.A., Moncalieri (IT)

( * ) Notice: Subject to any disclaimer, the term of this patent is extended or adjusted under 35 U.S.C. 154(b) by 913 days.

(21) Appl. No.: 13/482,494

(22) Filed: May 29, 2012

(65) Prior Publication Data

US 2012/0271246 A1 Oct. 25, 2012

Related U.S. Application Data

(63) Continuation of application No. PCT/IB2010/055430, filed on Nov. 25, 2010.

(30) Foreign Application Priority Data

Nov. 26, 2009 (IT) .............................. TO2009A0921

(51) Int. Cl.
*A61M 39/26* (2006.01)

(52) U.S. Cl.
CPC ....... *A61M 39/26* (2013.01); *A61M 2039/267* (2013.01)

(58) Field of Classification Search
CPC ............ A61M 39/26; A61M 2039/261; A61M 2039/262; A61M 2039/263; A61M 2039/266; A61M 2039/267; A61M 2039/268
See application file for complete search history.

(56) References Cited

U.S. PATENT DOCUMENTS

| 7,559,530 | B2 | 7/2009 | Korogi et al. | |
|---|---|---|---|---|
| 2003/0032940 | A1 | 2/2003 | Doyle | |
| 2005/0087715 | A1* | 4/2005 | Doyle | 251/149.1 |
| 2005/0151105 | A1 | 7/2005 | Ryan et al. | |
| 2006/0192164 | A1* | 8/2006 | Korogi et al. | 251/149 |
| 2008/0249508 | A1 | 10/2008 | Lopez et al. | |

FOREIGN PATENT DOCUMENTS

| EP | 1 834 665 A1 | 9/2007 |
|---|---|---|
| EP | 1 834 665 B1 | 2/2010 |
| JP | 10507946 | 8/1998 |

(Continued)

OTHER PUBLICATIONS

English machine-translation of WO 2009/118417 (dated Jun. 30, 2015).*

(Continued)

*Primary Examiner* — Kami A Bosworth
(74) *Attorney, Agent, or Firm* — Heslin Rothenberg Farley & Mesiti P.C.; Victor A. Cardona, Esq.

(57) ABSTRACT

A valved male luer connector includes a resilient hollow element enclosing a tubular member having an inlet portion and an outlet portion. A collar is axially displaceable to cause a stretching deformation of the resilient hollow element so as to open a cut of a terminal wall thereof adjacent to an initial end of the inlet portion of the tubular member. The collar has a containment axial appendage of the resilient hollow element up to close to the terminal wall thereof. A stop means for limiting the stretching deformation of the resilient hollow element is provided for in the zone close to the terminal wall thereof.

18 Claims, 7 Drawing Sheets

(56) References Cited

FOREIGN PATENT DOCUMENTS

| | | |
|---|---|---|
| JP | 2004275471 | 7/2004 |
| JP | 2008529680 | 8/2008 |
| WO | 9613301 A2 | 5/1996 |
| WO | 2006088858 A2 | 8/2006 |
| WO | 2008/057956 A2 | 5/2008 |
| WO | 2008/057956 A3 | 5/2008 |
| WO | 2009/118417 A1 | 10/2009 |

OTHER PUBLICATIONS

The Notification of Transmittal of the International Search Report and the Written Opinion of the International Searching Authority (PCT/ISA/220), along with the International Search Report (PCT/ISA/210), and the Written Opinion of the International Searching Authority (PCT/ISA/237) completed on May 2, 2011 and dated May 10, 2011.

* cited by examiner

VALVED MALE LUER CONNECTOR

CROSS REFERENCE TO RELATED APPLICATIONS

This application is a 371 national stage of PCT International Application No. PCT/IB2010/055430, filed on Nov. 25, 2010, and published in English on Jun. 3, 2011, as WO 2011/064738 A2, which claims priority to Italian Patent Application Number TO2009A000921 filed on Nov. 26, 2009, the entire disclosures of which are incorporated herein by reference.

FIELD OF THE INVENTION

The present invention generally refers to connectors for medical fluids, and more in particular regarding a valved male luer connector, designed to be connected to a female luer connector to open a flow passage through the two connectors.

PRIOR ART

Considering use thereof in the medical field, connectors thus made must be capable of guaranteeing a perfect closing in absence of the female connector, an instantaneous coupling during the coupling with the female connector, and an instantaneous return to the closed condition after the decoupling of the female connector.

In order to attain such effects, a valved male luer connector comprising a casing, a tubular member having an inlet portion with an initial end and an outlet portion, and a resilient hollow element secured to the casing and slidably axially enclosing the inlet of the tubular member was proposed in the U.S. Pat. No. 7,559,530 transferred to the Applicant. The resilient hollow element has a terminal wall having a cut and adjacent to the initial end of the inlet portion of the tubular member, and a collar is interposed between the casing and the resilient hollow element. The collar is axially displaceable, following thrust engagement by a female connector, to cause a stretching deformation of the resilient hollow element, with the consequent opening of the abovementioned cut and flow passage between the inlet portion and the outlet portion of the tubular member.

Thus, this valved male luer connector operates differently from the analogous prior art valve connectors, due to the stretching deformation instead of a compression of the resilient hollow element which defines, through the terminal wall thereof with the cut, the closing valve member.

Though fully efficient in the case wherein the connector is intended for disposable use or for a limited number of uses, this prior art connector reveals drawbacks in case of repeated opening and reclosing cycles. Such drawbacks are essentially due to the risk of an inadequate sealed reclosing by the terminal wall of the resilient hollow element, caused by burrs or even tears in the cut zone in turn due to a asymmetric diversions or deformations of the resilient hollow element during the stretching extension thereof, which could also have an impact on the subsequent correct elastic return to the non-deformed condition.

A further drawback of this prior art valved male luer connector lies in the possibility that the resilient hollow element, which is freely exposed outside in the closed condition, can be inadvertently or even intentionally deformed creating an undue and hazardous opening of the cut of the relative terminal wall.

SUMMARY OF THE INVENTION

The present invention has the object of improving the abovementioned connector known from the aforementioned document U.S. Pat. No. 7,559,530, and more in particular that of drastically reducing the risk of malfunctions due to incorrect deformations of the resilient hollow element, and the ensuing problems regarding safe and reliable closing of the cut of the terminal wall thereof.

A further object of the invention is that of preventing inadvertent or however undesired opening of the cut of the terminal wall of the resilient hollow element.

According to the invention, these objects are attained due to a valved male luer connector of the type defined in the preamble of claim 1, whose main characteristic lies in the fact that the collar interposed between the casing and the resilient hollow element has a containment axial appendage for said resilient hollow element up to substantial proximity of the terminal wall thereof.

This solution idea allows obtaining several important advantages.

Firstly, the containment action exerted by the axial appendage of the collar prevents uncontrolled or however incorrect deformations of the lateral wall of the resilient hollow element during the stretching deformation thereof, thus ensuring a perfect closing of the cut of the relative terminal wall even following repeated opening and reclosing cycles of the valve connector.

On the other hand, the presence of the axial appendage of the collar drastically reduces the risk of lacerations of the terminal wall of the resilient hollow element at the relative cut and, in case of a laceration, the propagation thereof is however limited or stopped.

The stretching deformation of the resilient hollow element is thus well controlled almost over the entire axial extension thereof comprised between the terminal wall thereof and the zone of the collar from which the relative containment axial appendage extends.

According to a preferred embodiment of the invention the lateral wall of the resilient hollow element has an outer radial flange axially facing towards the abovementioned containment axial appendage of the collar.

The abutment between such outer radial flange and the free end of the containment axial appendage of the collar allows, in the closed condition of the connector, further preventing undesired or inadvertent opening of the cut of the terminal wall of the resilient hollow element. Furthermore such radial flange advantageously allows providing the positive reclosing of such cut, following opening thereof by the female connector and the subsequent removal of the latter. such positive reclosing effect, determined by the axial thrust applied by the containment axial appendage of the collar against the outer radial flange of the terminal wall of the resilient hollow element, further contributes to guaranteeing the perfect closing of the connector even after repeated opening and reclosing cycles, additionally to the efficient control of the resilient deformation of the hollow element and of the relative terminal wall with the cut.

Such effect is further increased due to the fact that, according to a further advantageous characteristic of the invention, the tubular member has, close to the initial end of the inlet portion thereof, an outer annular groove within which an inner guiding projection of the resilient hollow element is slidably fitted.

The cooperation between such inner guiding projection of the resilient hollow element and the outer groove of the tubular member limits, substantially stop-means-like, the stretching deformation of the zone of the resilient hollow element close to the end wall thereof, hence further contributing to preventing risks of lacerations or tears in the zone of such cut.

With the aim of guaranteeing a gradual, and most stress-free possible, opening of the cut of the terminal wall of the resilient hollow element during the coupling between the valved male luer connector and a female connector, the abovementioned initial end of the inlet portion of the tubular member is conveniently formed with an outer annular rounded enlargement.

BRIEF DESCRIPTION OF THE DRAWINGS

Further characteristics and advantages of the invention shall be clear from the detailed description that follows, with reference to the attached drawings provided purely by way of non-limiting example, wherein.

DETAILED DESCRIPTION OF THE INVENTION

Figure 1:
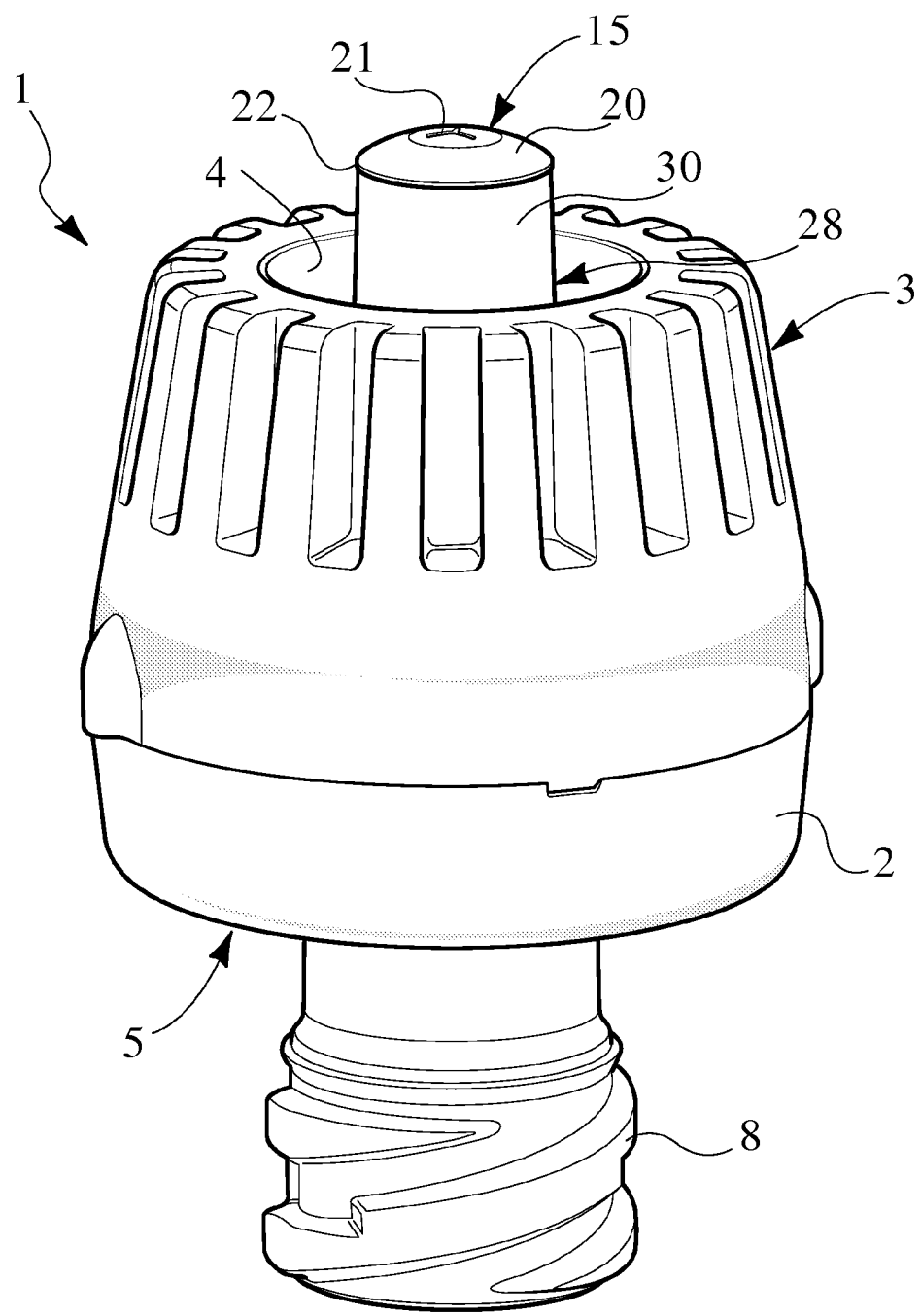
FIG. 1 is a schematic perspective view of a valved male luer connector according to the invention.

Initially referring to FIGS. 1 to 4, the valved male luer connector according to the invention comprises a casing 1 constituted a lower flange portion 2 permanently coupled to an upper hollow body 3 formed on the side opposite to the flange 2, with an internally threaded seat 4.

The flange 2 is in turn formed integrally and coaxially with a tubular member indicated in its entirety with 5, having an inlet portion 6 extended through the hollow body 3 projecting outside the respective threaded seat 4, and an outlet portion 7. The inlet portion 6, alongside other parts to be described hereinafter, defines with the threaded seat 4 a male lock luer connector designed to be engaged by a female connector, not illustrated in that per se known. For example, the female connector can be of the valve type described and illustrated in the patent application of EP-1834665A2 also on behalf of the Applicant.

The outlet portion 7 communicates with a tubular appendage 8 for example configured like a female lock luer connector, also integrally formed with the flange 2 and projecting at the rear part with respect to the casing 1.

The inlet 6 and outlet 7 portions are connected to each other through two series of separated radial passages 9, 10 whose mutual communication is controlled as clarified hereinafter.

The inlet portion 6 has an open initial end, indicated with 11, at which a rounded wall annular enlargement 12 delimiting—at the upper part—an outer annular groove 13 in turn delimited inside by a stop step 14 is formed.

A resilient hollow element, typically an elastomer or silicone rubber, including an annular base 16 secured in the casing 1 between the flange 2 and the body 3, a generally first cylindrical portion 17 connected to the base 16 through a generally conical part 18 diverging towards such first cylindrical portion 17, and a generally second cylindrical portion 19 slightly narrowed with respect to the first cylindrical portion 17 and having a terminal transverse wall 20 is indicated with 15.

The terminal wall 20 is centrally provided with a cut 21, for example linear or tricuspid-shaped like in the case of the illustrated example, normally closed due to the resilience characteristic of the resilient hollow element 15. An outer radial flange 22, whose function shall be clarified hereinafter, projects from the perimeter edge of the terminal wall 20.

The second cylindrical portion 19 of the resilient hollow element 15 is internally formed with an annular guiding projection 23, slidable within the groove 13 of the inlet portion 6 of the tubular member 5, between the annular enlargement 12 and the step 14.

The first cylindrical portion 17 is internally formed having at least one first, one second and one third annular sealing projection spaced from each other, respectively indicated with 24, 25 and 26, in slidable sealing contact on the tubular member 5.

The terminal wall 20 of the resilient hollow element 15 is usually arranged immediately above the initial end 11 of the inlet portion 6, with the cut 21 thereof kept closed. Such position corresponds to the closed condition of the valve connector, represented in FIGS. 1, 2 and 5, in which the communication between the radial passages 9 and 10 of the tubular member 5 are insulated from each other at least by the inner annular projection 24 of the resilient hollow element 15, hence the communication between the inlet portion 6 and the outlet portion 7, i.e. the flow passage through the connector, are hindered.

A collar interposed between the hollow body 3 of the casing 1 and the resilient hollow element 15 and constituting, as observable hereinafter, an actuator member designed to control the opening of the flow passage through the connector following the coupling thereof with the female luer connector, due to a stretching deformation of the resilient hollow element 15 is indicated with reference 28.

The collar 28 encloses the first cylindrical portion 17 of the resilient hollow element 15 and the lower portion 29 thereof is engaged in the conical portion 18 of such resilient hollow element 15.

According to the distinctive characteristic of the invention, the collar 28 is also provided with—at the upper part—a containment axial appendage 30 enclosing the second cylindrical portion 19 of the resilient hollow element 15 and it extends up to substantial proximity of the terminal wall 20 thereof. The free end of the containment appendage 30 axially faces towards the outer radial flange 22 of the terminal wall 20. The outer radial flange 22 extends radially outwardly at least to an outermost radial surface of the free end of the containment appendage 30.

The containment axial appendage 30 of the collar has an outer engagement surface of the female connector, for example—though not necessarily—a luer cone.

The valve connector according to the invention operates as follows.

Figure 2:
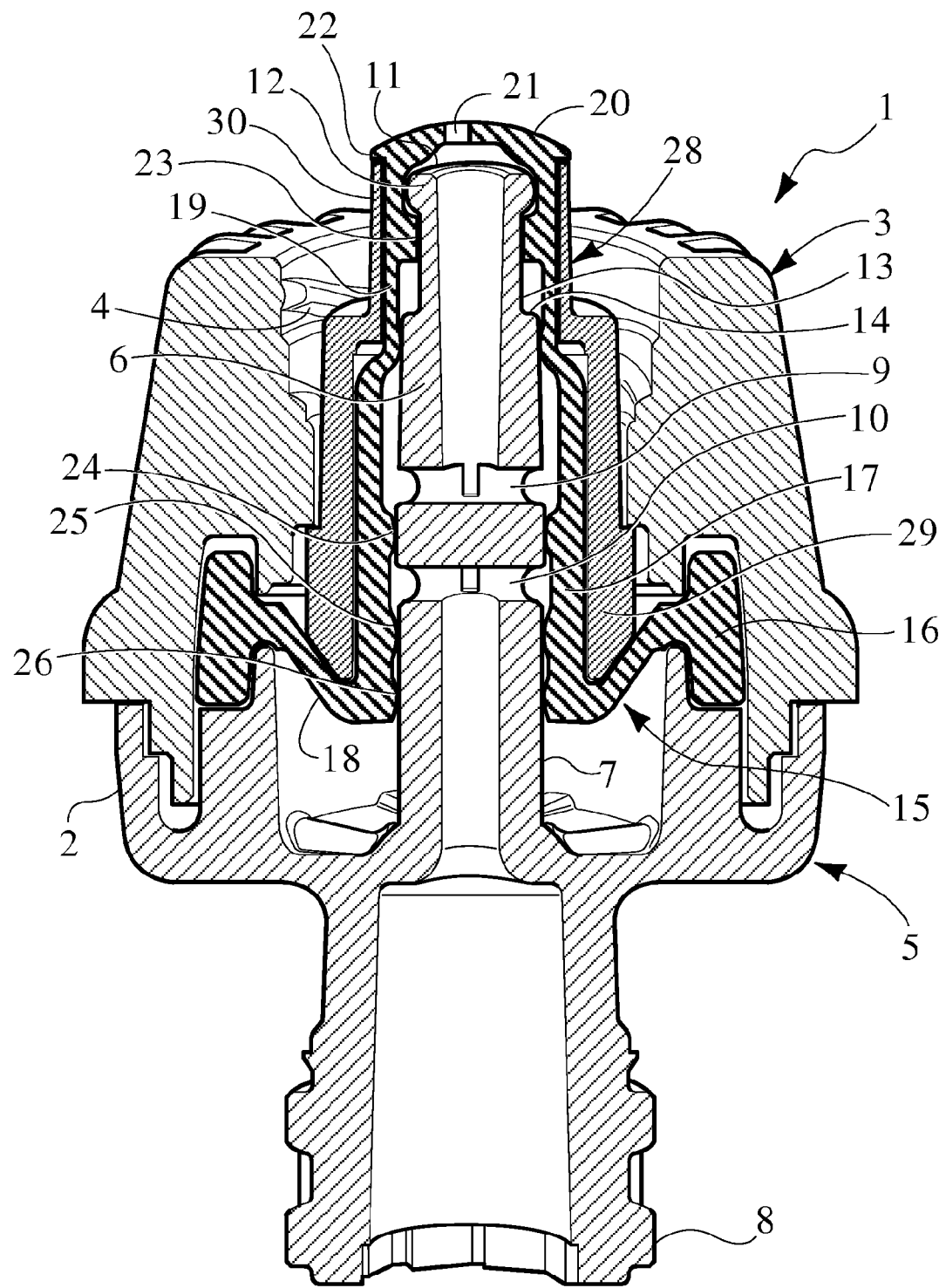
FIG. 2 is an axial sectional view of FIG. 1.
Figure 3:
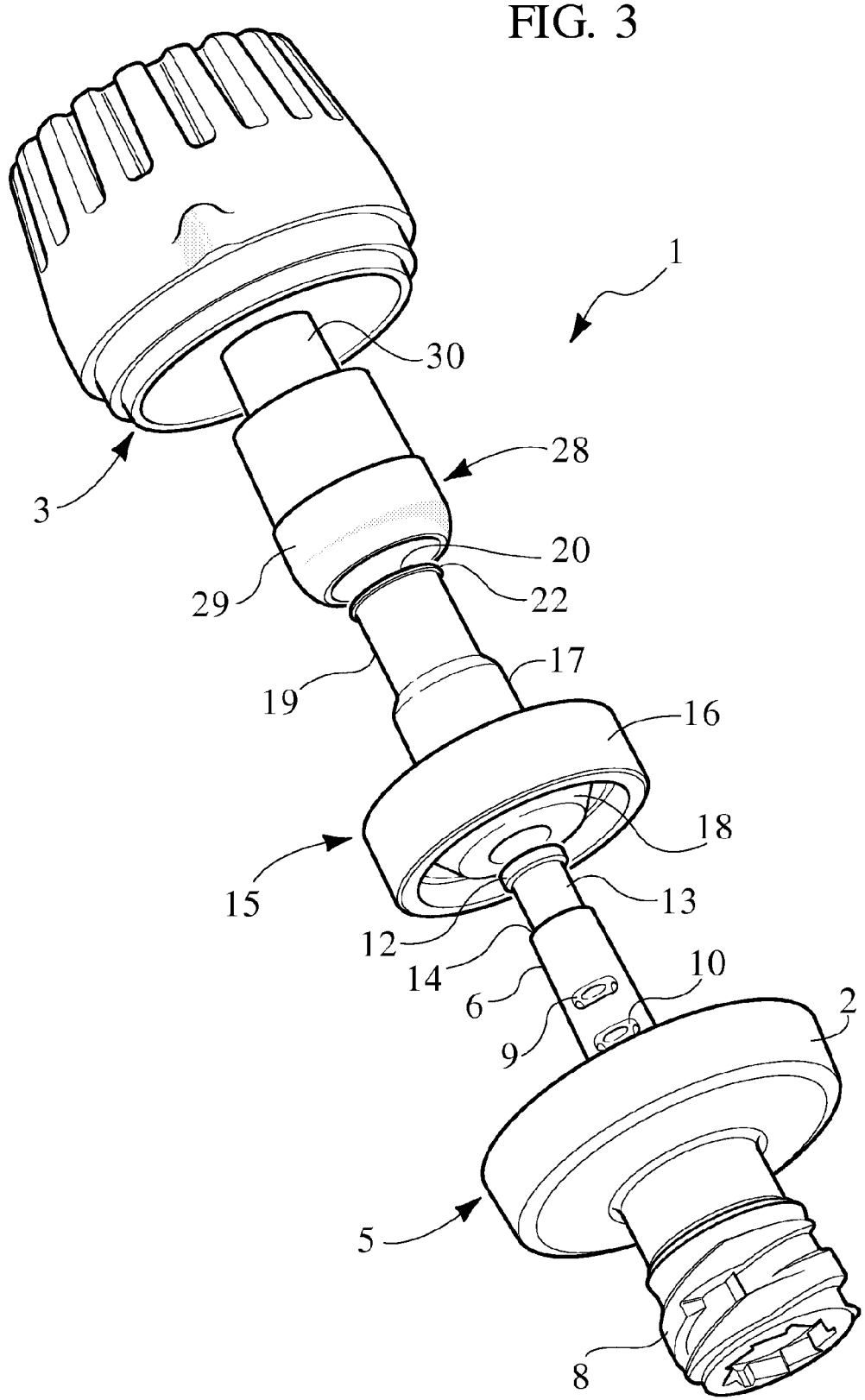
FIG. 3 is an exploded perspective view of the connector.
Figure 4:
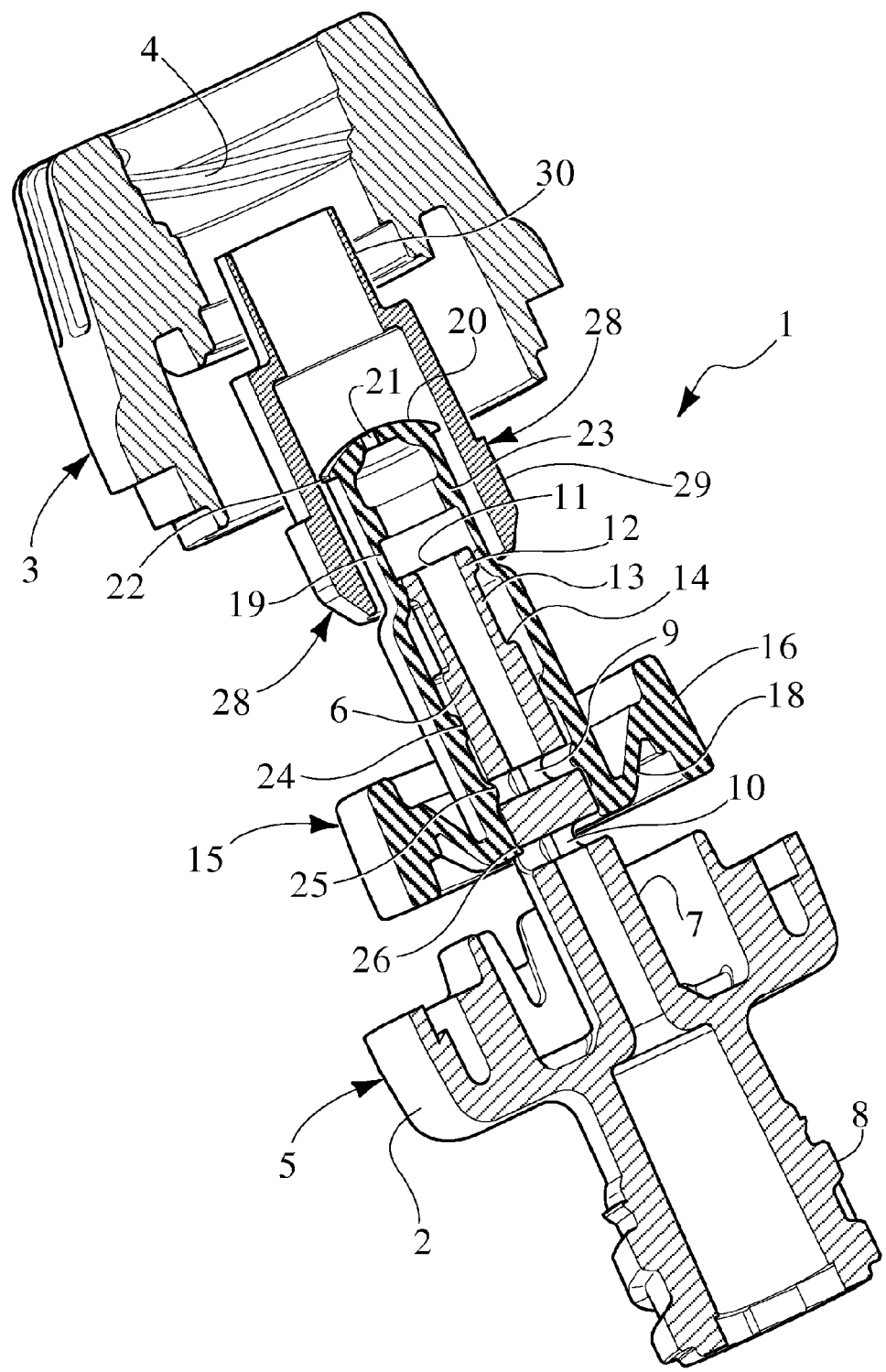
FIG. 4 is a sectional view of FIG. 3, and FIGS. 5, 6 and 7 are sectional schematic views analogous to FIG. 2 exemplifying respective different steps of operation of the valved male luer connector according to the invention.
Figure 5:
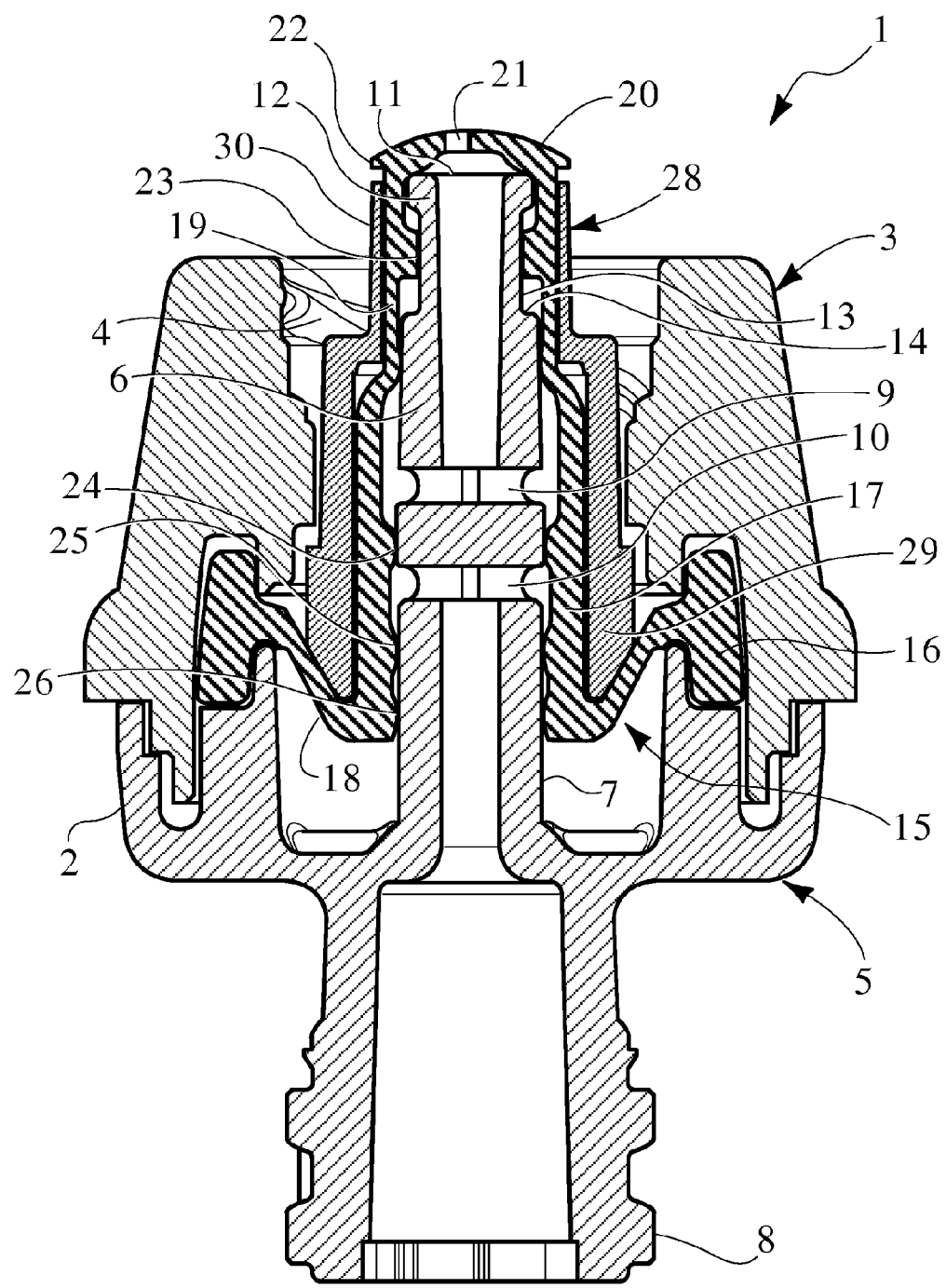

In the closed condition, as mentioned represented in FIGS. 1, 2 and 5, the cut 21 of the terminal wall 20 of the resilient hollow element 15 is closed and an inadvertent or however undesired opening thereof is hindered by the presence of the containment axial appendage 30, against which the outer radial flange 22 abuts in case of an attempt to push or deform the cylindrical portion 19 downwards with the terminal wall 20 tending to cause the opening of the cut 21.

Figure 6:
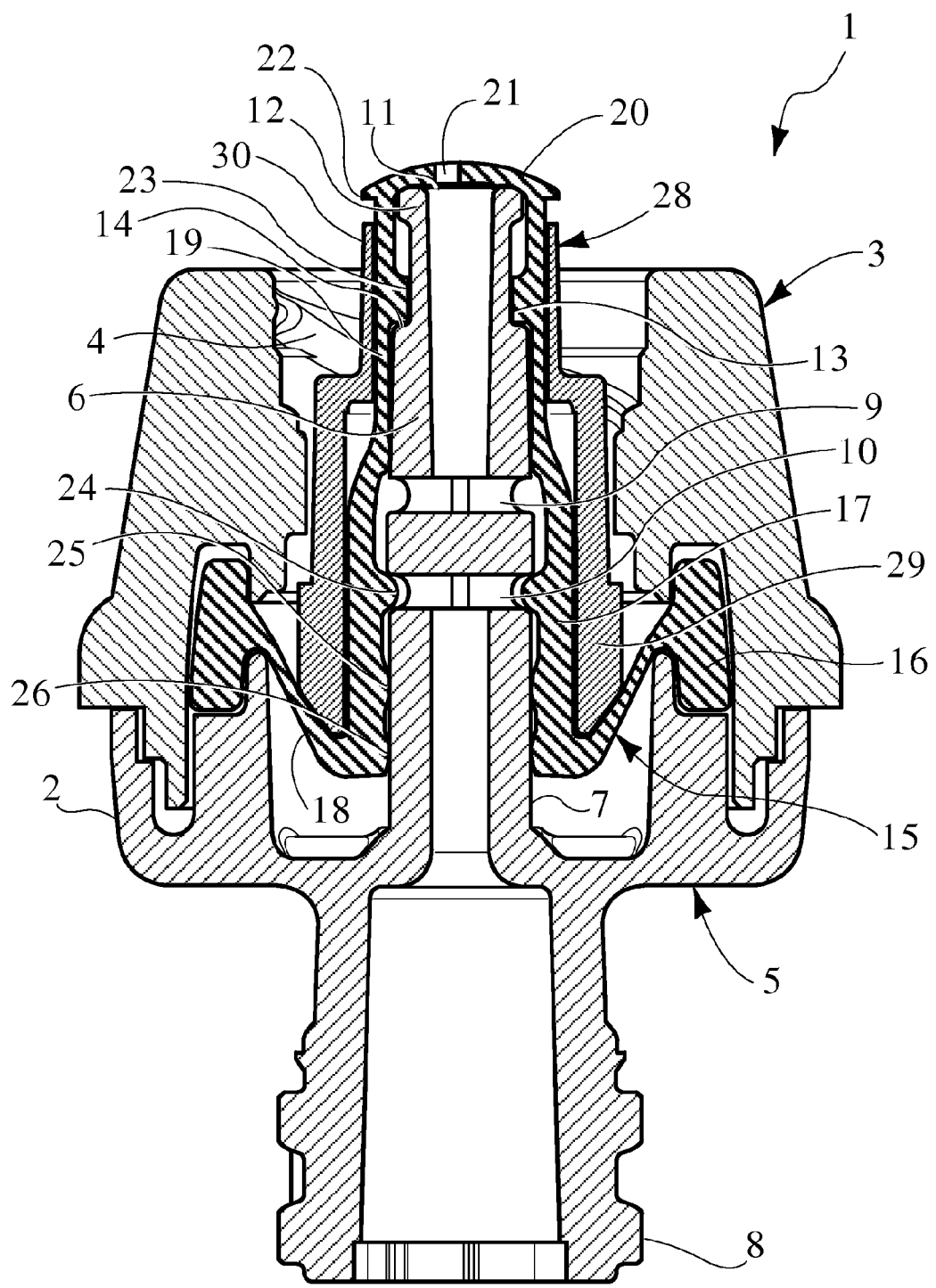

In order to provide the opening of the connector it is necessary to introduce and couple a female luer connector into the seat 4 of the body 3: due to such introduction the female connector, as mentioned not represented in the drawings but corresponding for example to that described and illustrated in the previously mentioned EP-1834665A2, axially engages the containment appendage 30 and thus applies an axial thrust on the collar 28, so as to push it in the direction of the outlet passage 7. Due to the interaction between the base 29 of the collar 28 and the conical portion 18, the resilient hollow element 15 is thus stretch resiliently deformed, pressing the inner surface of the terminal wall 20 against the initial end 11 of the inlet portion 6 of the tubular member 5. During this step, represented initially in FIG. 5 and then in FIG. 6, the inner guiding projection 23 of the resilient hollow element 15 translates along the groove 13, starting from the outer enlargement 12, until it stops against the stop step 14 as represented in FIG. 6. Simultaneously, the inner annular projection 24 of the resilient hollow element 15 moves downwards, due to the stretching deformation of the portion 17 thereof, until it frees the communication between the radial passages 9, 10, and thus between the inlet portion 6 and the outlet portion 7 of the tubular member 5. During this step, the cut 21 starts opening due to the interaction between the terminal wall 20 and the outer annular enlargement 12.

Figure 7:
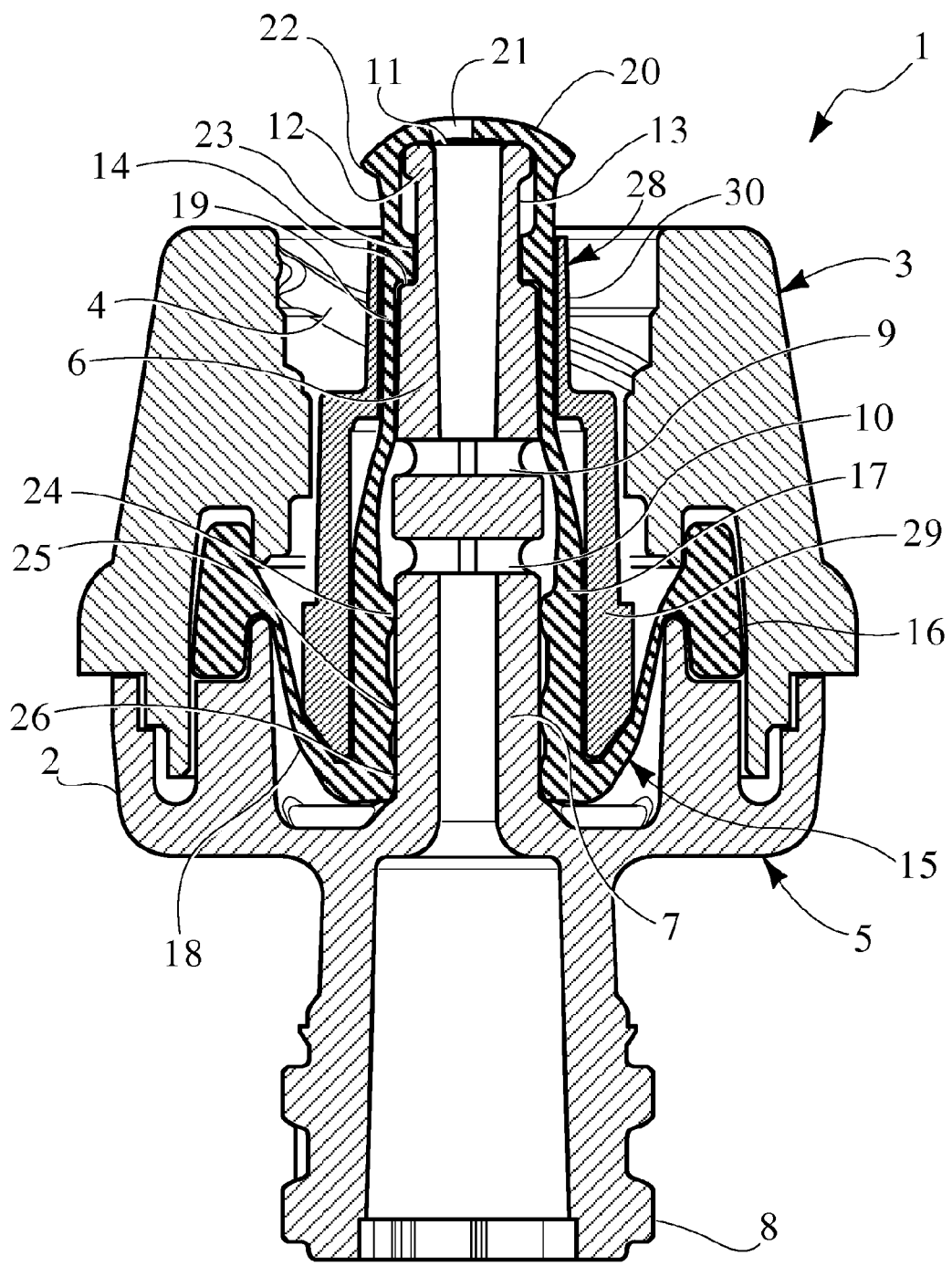

Following the complete opening of the female connector, and the further downward displacement of the collar 28 and thus the ensuing stretching deformation of the resilient hollow element 15, the further interaction between the terminal wall 20 and the annular enlargement 12 produces the complete opening of the cut 21 and, correspondingly, the complete opening of the flow passage between the inlet portion 6 and the outlet portion 7, as represented in FIG. 7.

The controlled stretching of the second cylindrical portion 19 of the resilient hollow element 15 prevents, due to the interaction between the inner guiding projection 23 and the groove 13, the risk of laceration of the cut 21. Furthermore, in the downward translation of the second cylindrical portion 19, up to the abutment of the inner guiding projection 23 against the step 14, the containment provided by the axial appendage 30 of the collar 28 prevents such portion 19 from diverting laterally, hence guaranteeing the subsequent correct return to the initial position following the decoupling of the female connector. In addition, such return is not obtained solely due to the elastic return of the hollow element 15 to the initial undeformed condition, but also due to the positive action provided by the axial appendage 30. Actually, the interaction between the free end of the axial appendage 30 and the outer radial flange 22 of the terminal wall 20 safely and reliably restores the undeformed closed condition of the cut 21.

Thus, the description outlined above clearly shows that the presence of the containment axial appendage 30 and also that of the outer groove 13 with the stop step 14 cooperating with the inner guiding projection 23, as well as that of the outer radial flange 22 and that of the enlargement 12, allows attaining the improved control of the opening and reclosing of the connector according to the invention, thus preventing risks of malfunction even in case of repeated actuations.

Obviously, the construction details and the embodiments may widely vary with respect to what has been described and illustrated, without departing from the scope of protection of the present invention as defined in the claims that follow.

The invention claimed is:

1. A valved male luer connector comprising:
a casing,
a tubular member having an inlet portion with an initial end and an outlet portion,
a resilient hollow element secured to the casing and enclosing the tubular member,
said resilient hollow element having a terminal wall adjacent to said initial end of the inlet portion of the tubular member and having a cut,
a collar interposed between the casing and the resilient hollow element,
said resilient hollow element axially displaceable, following thrust engagement by a female connector, to cause a stretching deformation of said resilient hollow element with a consequent opening of said cut and a flow passage between said inlet portion and said outlet portion of the tubular member, and
said collar comprising a containment member forming an axial appendage thereof and extending adjacent said terminal wall of said hollow element, wherein said collar causes a stretching deformation of said resilient hollow element during opening of said cut,
said terminal wall of the resilient hollow element having an axially facing surface of an outer radial flange axially facing towards an axial end of said axial appendage of said collar, said outer radial flange extending radially outwardly at least to an outermost radial surface of a first end of said axial appendage of said collar, said first end of said axial appendage comprising an outermost radial surface having a smaller radial diameter than an outermost surface of said collar located at an opposite end of said collar relative to said axially facing surface.

2. The connector according to claim 1, wherein said tubular member has a stop means designed to limit said stretching deformation of a portion of said resilient hollow element close to said terminal wall.

3. The connector according to claim 2, wherein said tubular member has, close to said initial end of the inlet portion, an outer annular groove ending at said stop means and within which an inner guiding projection of said resilient hollow element is slidably fitted.

4. The connector according to claim 3, wherein said outer annular groove is delimited, in substantial correspondence of said initial end of the inlet portion, by an outer annular rounded enlargement.

5. The connector according to claim 4, wherein said inlet portion and said outlet portion of said tubular member are connected to each other through mutually separated radial passages and in that said resilient hollow element is provided with inner annular projections controlling communication between said radial passages.

6. The connector according to claim 4, wherein said axial appendage of said collar has an outer engagement surface for a female connector.

7. The connector according to claim 3, wherein said inlet portion and said outlet portion of said tubular member are connected to each other through mutually separated radial passages and in that said resilient hollow element is provided with inner annular projections controlling communication between said radial passages.

8. The connector according to claim 3, wherein said axial appendage of said collar has an outer engagement surface for a female connector.

9. The connector according to claim 2, wherein said inlet portion and said outlet portion of said tubular member are connected to each other through mutually separated radial passages and in that said resilient hollow element is provided with inner annular projections controlling communication between said radial passages.

10. The connector according to claim 2, wherein said axial appendage of said collar has an outer engagement surface for a female connector.

11. The connector according to claim 1, wherein said inlet portion and said outlet portion of said tubular member are connected to each other through mutually separated radial passages and in that said resilient hollow element is provided with inner annular projections controlling communication between said radial passages.

12. The connector according to claim 11, wherein said axial appendage of said collar has an outer engagement surface for a female connector.

13. The connector according to claim 1, wherein said appendage has an outer engagement surface for a female connector.

14. The connector according to claim 1 wherein said axially facing surface engages said axial end of said axial appendage of said collar.

15. The connector according to claim 1 wherein said axially facing surface abuts said axial end of said axial appendage of said collar.

16. The connector according to claim 1 wherein said outer radial flange extends to an outer radial extent of said collar.

17. A valved male luer connector comprising:
a casing,
a tubular member having an inlet portion with an initial end and an outlet portion,
a resilient hollow element secured to the casing and enclosing the tubular member,
said resilient hollow element having a terminal wall adjacent to said initial end of the inlet portion of the tubular member and having a cut;
a collar interposed between the casing and the resilient hollow element,
said resilient hollow element axially displaceable, following thrust engagement by a female connector, to cause a stretching deformation of said resilient hollow element with a consequent opening of said cut and a flow passage between said inlet portion and said outlet portion of the tubular member; and
said collar comprising a containment member forming an axial appendage thereof and extending adjacent said terminal wall of said hollow element, wherein said collar causes a stretching deformation of said resilient hollow element during opening of said cut;
said terminal wall of the resilient hollow element having an axially facing surface of an outer radial flange axially facing towards an axial end of said axial appendage of said collar, said outer radial flange extending further radially outwardly than an inner radial surface of said collar;
said tubular member having a stop step to limit the stretching deformation of a portion of said resilient hollow element close to said terminal wall;
said tubular member having an outer annular groove ending at said stop step, and
an inner guiding projection of said resilient hollow element slidably fitted within said groove; and
said resilient hollow element comprising a first cylindrical portion surrounding said outlet portion of said tubular member and a second cylindrical portion surrounding said inlet portion of said tubular member, said guiding projection projecting inwardly from said first second cylindrical portion and being surrounded by said axial appendage, said first cylindrical portion having an outside diameter different from said second cylindrical portion.

18. The connector of claim 17 wherein said outer annular groove is bounded, in substantial correspondence of said initial end of the inlet portion, by an outer annular rounded enlargement.

\* \* \* \* \*